United States Patent
Mazumder et al.

(10) Patent No.: US 9,752,988 B2
(45) Date of Patent: Sep. 5, 2017

(54) IN-SITU IDENTIFICATION AND CONTROL OF MICROSTRUCTURES PRODUCED BY PHASE TRANSFORMATION OF A MATERIAL

(75) Inventors: Jyotirmoy Mazumder, Ann Arbor, MI (US); Lijun Song, Ann Arbor, MI (US); Cunshan Wang, Dalian (CN)

(73) Assignee: The Regents of the University of Michigan, Ann Arbor, MI (US)

( * ) Notice: Subject to any disclaimer, the term of this patent is extended or adjusted under 35 U.S.C. 154(b) by 1185 days.

(21) Appl. No.: 13/159,955

(22) Filed: Jun. 14, 2011

(65) Prior Publication Data

US 2012/0177810 A1   Jul. 12, 2012

Related U.S. Application Data

(60) Provisional application No. 61/354,286, filed on Jun. 14, 2010.

(51) Int. Cl.
B23K 26/32 (2014.01)
B23K 26/20 (2014.01)
G01N 21/71 (2006.01)

(52) U.S. Cl.
CPC ............................. *G01N 21/718* (2013.01)

(58) Field of Classification Search
CPC .... B23K 26/32; B23K 26/322; B23K 26/206; B23K 26/20; B23K 20/00; B23K 15/00; B23K 15/10
USPC ........... 219/121.64, 121.63, 121.83, 121.85, 219/121.66, 121.65
See application file for complete search history.

(56) References Cited

U.S. PATENT DOCUMENTS

| 5,659,479 A * | 8/1997 | Duley et al. ................. 700/166 |
| 6,762,836 B2 * | 7/2004 | Benicewicz ......... G01N 21/718 356/237.3 |
| 7,586,061 B2 * | 9/2009 | Hoebel et al. ........... 219/121.83 |
| 2002/0144984 A1 * | 10/2002 | Mori ..................... B23K 26/03 219/121.64 |
| 2005/0126709 A1 * | 6/2005 | Takayama et al. ...... 156/345.25 |
| 2005/0158886 A1 * | 7/2005 | Tanaka et al. ................ 438/8 |

(Continued)

FOREIGN PATENT DOCUMENTS

| JP | 11188489 | 7/1999 |
| JP | 2001170787 | 6/2001 |

OTHER PUBLICATIONS

International Search Report for PCT/US2011/040308, Feb. 17, 2012, 3 pages.

(Continued)

*Primary Examiner* — Michael Laflame, Jr.
(74) *Attorney, Agent, or Firm* — Reising Ethington P.C.

(57) ABSTRACT

A microstructure detector and in-situ method for real-time determination of the microstructure of a material undergoing alloying or other phase transformation. The method carried out by the detector includes the steps of: (a) detecting light emitted from a plasma plume created during phase transformation of a material; (b) determining at least some of the spectral content of the detected light; and (c) determining an expected microstructure of the transformed material from the determined spectral content. Closed loop control of the phase transformation process can be carried out using feedback from the detector to achieve a desired microstructure.

17 Claims, 8 Drawing Sheets

(56) References Cited

U.S. PATENT DOCUMENTS

| | | | |
|---|---|---|---|
| 2006/0054607 A1* | 3/2006 | Wu et al. | 219/121.83 |
| 2006/0279731 A1* | 12/2006 | Beyer | G01J 3/1809 |
| | | | 356/318 |
| 2007/0296967 A1* | 12/2007 | Gupta | G01J 3/2889 |
| | | | 356/318 |
| 2008/0210674 A1* | 9/2008 | Mazumder | B23K 26/032 |
| | | | 219/121.83 |
| 2008/0223832 A1* | 9/2008 | Song et al. | 219/121.66 |
| 2008/0296270 A1* | 12/2008 | Song et al. | 219/121.63 |
| 2009/0120581 A1* | 5/2009 | Qin et al. | 156/345.24 |
| 2010/0133247 A1* | 6/2010 | Mazumder et al. | 219/121.83 |

OTHER PUBLICATIONS

Written Opinion for PCT/US2011/040308, Feb. 17, 2012, 3 pages.

J. Mazumder et al., "Closed Loop Direct Metal Deposition: Art to Part," Optics and Lasers in Engineering 34, 397-414, 2000, pp. 1-18.

Dmitri V. Louzguine et al., "High Strength and Ductile Binary Ti-Fe Composite Alloy," Journal of Alloys and Compounds 384, L1-L3, 2004, pp. 1-3.

J. Das et al., "Bulk Ultra-Fine Eutectic Structure in Ti-Fe-Base Alloys," Journal of Alloys and Compounds 434-435, 28-31, 2007, pp. 1-4.

C. S. Wang et al., "Laser-Induced Self-Propagating Reaction Synthesis of Ti-Fe Alloys," Journal of Material Science, 43, 218-221, 2008, pp. 1-4.

Haitham El Kadiri et al., "Development of a Ti-based Alloy: Design and Experiment," Jom-Us, 60-66, 2009, pp. 1-7.

Igor B. Gornushkin et al., "Line Broadening Mechanisms in the Low Pressure Laser-Induced Plasma," Spectrochimica Acta B 54, 1207-1217, 1999, pp. 1-11.

* cited by examiner

IN-SITU IDENTIFICATION AND CONTROL OF MICROSTRUCTURES PRODUCED BY PHASE TRANSFORMATION OF A MATERIAL

CROSS-REFERENCE TO RELATED APPLICATION

This application claims the benefit of U.S. Provisional Application No. 61/354,286, filed Jun. 14, 2010, the entire contents of which are hereby incorporated by reference.

STATEMENT OF FEDERALLY-SPONSORED RESEARCH

This invention was made with government support under N00014-07-1-1032 awarded by the United States Navy Office of Naval Research. The government has certain rights in the invention.

TECHNICAL FIELD

This invention relates generally to phase transformation processes for metals and other materials and, more particularly, for sensors and techniques used to analyze the phase transformation process in real time.

BACKGROUND OF THE INVENTION

Service performances of all materials are generally determined by developing structure-property relationships. For example, the service performance and properties of a material made by a phase transformation process generally depend on the resulting microstructure of the transformed material. Phase transformation processes can include laser cladding, laser alloying, laser welding, laser melt quenching as well as such processes carried out using non-laser sources of energy (e.g., electron-beam and other techniques for applying sufficiently high localized heat to carry out the desired phase transformation process). The materials with which the disclosed invention can be used are typically metal materials; that is, materials comprising a single, pure elemental metal, binary, tertiary, and other plural combinations of different elemental metals, as well as combinations of one or more metals with other non-metals. However, ceramics and other non-metal materials can also be formed by phase transformation into varying microstructures.

Presently, known methods for determining the microstructure of a material resulting from a phase transformation process are mostly a postmortem analysis where a materials scientist takes a solidified piece of the material and carries out a polishing-etching process to determine different phases by Optical and Scanning Electron Microscopes (SEM). Then, often a post processing is adapted to create the desired microstructure for desired properties. In-situ identification of phase formation during synthesis has the possibility of saving a significant amount of human time and capital resource for materials and industry. For researchers, it could provide material scientists with a repeatable process for the synthesizing materials with a desired microstructure.

US Patent Application Publication No. 2010/0133247 A1, entitled "Monitoring of a Welding Process," includes additional information concerning the components and steps used for collecting, processing, and utilizing the light emitted from the plasma during phase transformation. The complete content of US Patent Application Publication No. 2010/0133247 A1 is hereby incorporated by reference.

SUMMARY OF THE INVENTION

In accordance with one aspect of the invention, there is provided a method of determining a microstructure of a material during phase transformation of the material. The method includes the steps of: (a) detecting light emitted from a plasma plume created during phase transformation of a material; (b) determining at least some of the spectral content of the detected light; and (c) determining an expected microstructure of the transformed material from the determined spectral content.

In accordance with another aspect of the invention, there is provided a method of controlling the phase transformation of a material. The method includes the steps of: (a) initiating a phase transformation of a material; (b) detecting light emitted from a plasma plume created during the phase transformation; (c) determining at least some of the spectral content of the detected light; and (d) producing a desired microstructure from the phase transformation by controlling one or more process parameters based on the determined spectral content.

In accordance with yet another aspect of the invention, there is provided a microstructure detector for use during phase transformation of a material. The detector includes a light collector oriented to receive light emitted from a plasma plume created during phase transformation of a material, a sensor that receives the light from the light collector, and a computing device that receives from the sensor spectral data indicative of at least some of the spectral content of the received light. The computing device operates to determine an expected microstructure of the transformed material from the received spectral data.

BRIEF DESCRIPTION OF THE DRAWINGS

Preferred exemplary embodiments of the invention will hereinafter be described in conjunction with the appended drawings, wherein like designations denote like elements, and wherein.

DETAILED DESCRIPTION OF THE ILLUSTRATED EMBODIMENTS

Described below are exemplary embodiments of an apparatus and method for in-situ phase identification during the synthesis process where plasma is present during synthesis. Also described is a method and system for feedback control of the phase transformation process to obtain a desired microstructure based on sensed spectral content of the light emitted from the plasma. In the embodiments described herein, identification and control of the formed microstructure during the phase transformation process is based generally on analysis of the spectral content of the light emitted from the plasma plume that is created during the phase transformation. For example, processes such as laser or electron-beam cladding, alloying, and welding involve the injection of high amounts of localized energy that create a plasma plume as one or more materials are phase transformed, usually from a solid feedstock or powder into a melt pool that then solidifies into a particular microstructure as it cools. Using the methods and apparatuses disclosed herein, the resulting microstructure can be predicted based on one or more spectral parameters derived from the spectral content of the light emitted from the plasma plume. For phase transformations that do not generate a plasma, an interrogating laser or other energy injector can be used to create a plasma with a Laser Induced Breakdown Spectroscopy (LIBS) then used to determine the phase of the transformed material and hence its microstructure.

Determination of microstructure can be accomplished based on a discovered correlation between one or more spectral parameters of the light emitted from the plasma and the resulting phase of the transformed material. This relationship has been experimentally confirmed for various binary alloys as will be described in greater detail below. For at least these binary combinations of different metals, spectral line intensity ratios, electron temperature, and electron density have each been found to demonstrate a deterministic relationship to the resulting microstructure of the transformed material, thereby allowing prediction of the resulting microstructure from one or more of these parameters. This information can also be used in manufacturing operations for closed loop process control to obtain a repeatable, desired microstructure for the manufactured part.

During laser material interaction, the vaporized material, containing neutral atoms, ions, electrons etc., is known as a laser-produced plasma plume and expands away from the melting pool surface. Any process which creates plasma will have presence of atoms, ions and electrons. During the laser cladding process, powders of different elements are melted into the molten pool and solidify onto the substrate. Different elemental combinations will experience different phase changes and form into different microstructures, depending on the composition, cooling rate and heat treatment. There exists a strong correlation between the physical parameters of a plasma plume and the final microstructures. It has therefore been found that the spectral line acquired from the plasma immediate prior to solidification can be a valid indicator for the crystal structure. Electron population of different energy state or the transition probability of the emission lines, affects the plasma parameters. This relationship can be used to predict the microstructure from the plasma characterization.

Since the laser cladding process uses relatively low laser intensities, the irradiated plasma plume can have resolved atomic emission lines from different elements, which are typically broadened to the Lorentz or Voigot profile depending on neutron, ion and electron interactions. The parameters obtainable from the plasma can be determined in several ways, including from an intensity ratio of the ions or atoms emission lines, from a FWHM (Full Width Half Maxima) of the line profile or from a Boltzmann plot. The short wavelength part of a broad-band radiation spectrum also gives information about the temperature of the plasma.

Based on plasma spectroscopy theory that supplements the approach discussed herein, the following assumptions are made for spectroscopic analysis: (i) optically thin plasma; local thermal equilibrium; and McWhirter criterion. These assumptions indicate that the plasma produced during laser cladding will have particles with Maxwellian energy distributions and the electron-electron collisional processes will dominate over radioactive ones.

The electron transition from an upper energy level $E_m$ to a lower energy level $E_n$ will produce an energy quantum $hv_{mn}$. Here h is the plank constant and $v_{mn}$ is the frequency of the photon. The relative intensity of the emission line $I_{mn}$ can be evaluated by:

$$I_{mn} \propto N_m A_{mn} h v_{mn} \qquad (1)$$

where $N_m$ is the population of the upper state. $A_{mn}$ is the transition probability.

For locally thermodynamic equilibrium (LTE) state, the population of upper state satisfies the Boltzmann law, which takes the form of $$\frac{N_m}{N} = \frac{g_m}{z(T)} \exp\left(\frac{-E_m}{kT}\right) \qquad (2)$$

where N is the total density of a state; z (T) is the partition function of the element; $g_m$ is the statistical weight; k is the Boltzmann constant, and T is the electron temperature. Introducing Eq. (2) into Eq. (1), a linear relationship between $\ln(I_{mn}\lambda_{mn}/g_m A_{mn})$ and $E_m$ can be obtained:

$$\ln\left(\frac{I_{mn}\lambda_{mn}}{g_m A_{mn}}\right) \propto \ln\left(\frac{Nhc}{z(T)}\right) - \frac{1}{kT}E_m \qquad (3)$$

The electron temperature can be calculated from the slope of this linear function (Eq. (3)) by generating a Boltzmann plot.

The electron density is normally determined from the line broadening. Major line broadening mechanisms are Stark broadening, Doppler broadening and pressure broadening. The Stark line broadening is due to the collision of charged species and can be fitted into a Lorentz function. Full width half maximum (FWHM) of Doppler broadening can be estimated using the Maxwellian distribution. The pressure broadening due to the frequency disturbance by the interaction of the radiating atoms with the surrounding particles can be estimated from a simplified model with semi-classical picture. However, both Doppler broadening and pressure broadening effect are small compared to Stark broadening. Therefore, the contribution of the Stark broadening is dominant.

Since the contribution of the ionic broadening is very small, the Stark broadening is mainly due to the electron contributions, which can be expressed by full width half maximum (FWHM) $\Delta\lambda$ as $$\Delta\lambda = 2\omega(N_e/10^{16}), \quad (4)$$

where $\omega$ (nm) is the electron impact width parameter and $N_e (\text{cm}^{-3})$ is the electron density. The electron density can be obtained using Eq. (4) by fitting the spectral line to Lorentz function and obtaining the FWHM of the fitted line.

To validate the local thermodynamic equilibrium (LTE) condition, McWhirter criterion can be used:

$$N_e \geq 1.6 \times 10^{12} T^{1/2} (\Delta E)^2 \quad (5)$$

where $\Delta E$ (eV) is the largest energy gap in the atomic energy level system.

Given the above theory of the relationship between the spectral content of the emitted plasma radiation and resulting microstructure, the following discussion details a sensor system and closed loop control system for the identification and production of a desired microstructure formed by a phase transformation process. Results of a laser cladding process for producing binary metal alloys that demonstrates the above-described correlations are also discussed below. However, as the description proceeds, it will be appreciated that the disclosed methods and apparatuses can be adapted by those skilled in the art for use with a wide variety of metals, ceramics, and other materials, including singular, binary, tertiary, and other plural combinations of elements and other materials.

For laser cladding, there are three general approaches for alloying materials together: a) the cladding head is moving and the substrate is fixed; b) the substrate is moving and cladding head is fixed and c) both cladding head and the substrate are moving. For each of these, the collecting optics of the sensor may be attached to cladding head so that it has a fixed position and orientation relative to the cladding process.

Figure 1:
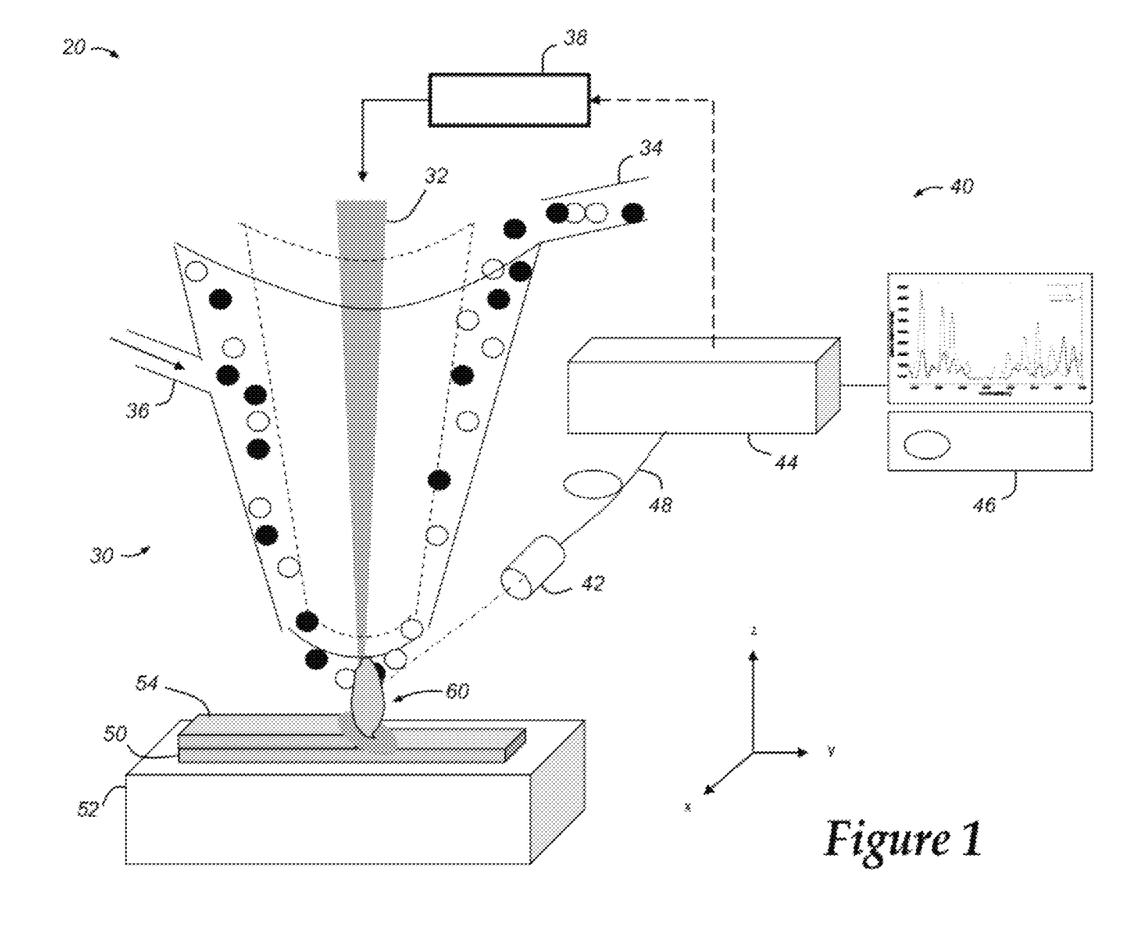
FIG. 1 is a diagram showing a laser cladding process with a microstructure detector constructed and used in accordance with an embodiment of the invention.

FIG. 1 diagrammatically depicts an embodiment of a method and system 20 that can be used to determine microstructure of a material undergoing a phase transformation using the techniques described herein. The system 20 generally includes three portions: tooling 30 which for example can be an end-effector controlled by robotics or other automation; a microstructure detector 40; and a workpiece 50 that is disposed on a substrate 52. The particular example shown is directed to laser cladding using a flow of metal powder applied to the workpiece 50 to thereby produce an alloyed component having a cladding layer 54 over the workpiece 50. It will be appreciated that the microstructure detector and method disclosed herein can be used for other alloying and other material processes that involve phase transformation. The materials, techniques, and tooling involved in laser cladding and other material processes involving material phase transformation are known to those skilled in the art and need not be detailed here. The tooling 30 can be implemented as known in the art using a laser beam 32 with a source of cladding powder 34 and a shielding gas 36. A controller 38 is used to control various process parameters such as the laser beam 32, powder material flow rate, and/or others. Detector 40 generally includes a light collector 42, a sensor 44, and a computer 46 or other computing device. The light collector 42 is constructed and arranged to receive light emitted from a plasma plume 60 emitted from the laser cladding or other material process. A fiber optic cable 48 connects the light collector 42 to the sensor 44 using, for example, SMA connectors (not shown). As discussed below, sensor 44 includes a photo-detector that outputs spectral data indicative of at least some of the spectral content of the collected (received) light. That data is used by the computing device 46 to determine the microstructure produced by the laser cladding process. In the illustrated embodiment, sensor 44 comprises a spectrometer.

For the purposes of microstructure identification, there are three general steps involved. The first is the collecting of light emitted from the plasma plume 60 created during the phase transformation process (either inherently by the process itself or by way of an interrogating laser). Light collection can be done using light collector 42 which can be a focusing or collimating lens. The collimating lens can be a tunable collimating assembly along with an SMA connector for coupling to the fiber optic cable 48. The fiber optic cable carries the received light to the spectrometer 44 that includes one or more photo-detectors that together are capable of determining ultraviolet and visible spectral content of the received light. The fiber optic cable 48 can be a polarization-resistant fiber with a UV/SR-VIS 190-800 nm transmission window is used to deliver the light to the photo detectors.

The second step is to determine the spectral content of the received light by the photo-detectors. This can be done using a spectrometer 44 that is sensitive to the ultraviolet and visible light regions, although spectral lines outside of this region can be used as well if they can be used to derive one or more spectral parameters indicative of microstructure. The spectral band of interest for a particular phase transformation process can depend on the distribution of possible emission lines from the material(s) being transformed (e.g., powder 34 and workpiece 50), and may involve a tradeoff between the resolution of measurement and the width of the detection range. For known material(s) having a narrow spectral range, the spectrometer may be replaced by an interference filter that is used as the sensor 44.

The third step involves determining an expected or predicted microstructure based on the spectral content determined by the sensor. This is done using the computing device 46 which can be a programmed computer that receives spectral data outputted by the sensor 44 and processes it in real time to compare the spectral data, representing one or more spectral parameters, with known spectral values representing one of a number of different potential microstructures. This can be done in successive groups of data, each representing a particular time slot of measurement. As discussed above, the spectral parameters used can be, for example, any one or more of the following: relative spectral line intensities, electron temperature, and electron density. In one embodiment, all three parameters are used to help reduce the possibility of error in the microstructure identification.

Figure 2:
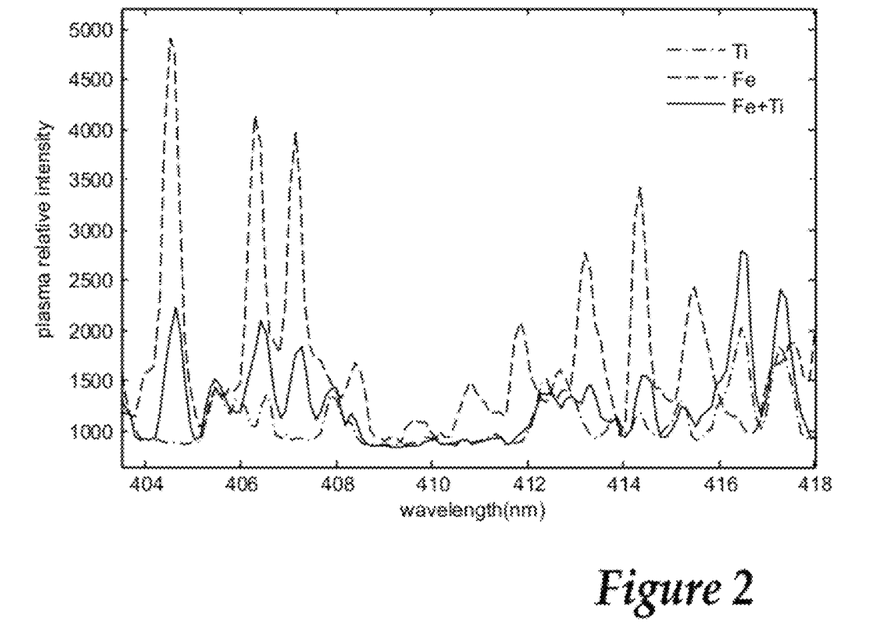
FIG. 2 shows plasma radiation from 404 nm to 418 nm during direct metal deposition of pure titanium, pure iron, and 50% titanium and 50% iron mixtures.

This processing of the spectral data can first involve identifying the spectral lines irradiating from the different elements. An example of this is shown in FIG. 2 for pure Ti and pure Fe irradiations. Then, the spectral parameters such as the line intensities, plasma temperatures and electron densities will be calculated for each time slot. These results are then compared with known values to predict the microstructure.

These results can further be used to provide closed-loop feedback to the phase transformation controller 38, such as shown by the dashed line in FIG. 1 and as used by the welding controller shown in the incorporated US Patent Application Publication No. 2010/0133247 A1. The same system components disclosed in that publication can be used for the system discussed herein, with suitable programming of the computer to determine the spectral parameters and determine from them the microstructure of the transformed material(s).

The following examples describe three pairs of binary alloys that were manufactured from a direct metal deposition process with changed elemental ratios used in each example to demonstrate the correlation between spectral content and resultant microstructure. For each binary alloy, the line intensity ratio, plasma temperature and electron density were calculated and compared to the composition ratios.

Example 1

Ti—Fe Alloy

For binary Fe—Ti alloying process, element powders of Ti (99.99% purity, −200 mesh) and Fe (99.90% purity, −200 mesh) were blended with different atomic ratios (Ti/Fe=75.9/24.1, 73.1/26.9, 70.8/29.2, 65.5/34.4 and 59.8/40.2) around the eutectic composition point (70.8/29.2 atomic ratio). The laser beam size was 0.5 mm. The laser power was 500 W. Powder flow rate was 2.1 g/min. Scanning speed was 365 mm/min. z increment for each next layer was 0.25 mm. The plasma collection was performed after the second layer, in order to eliminate the effect from the substrate.

Figure 3:
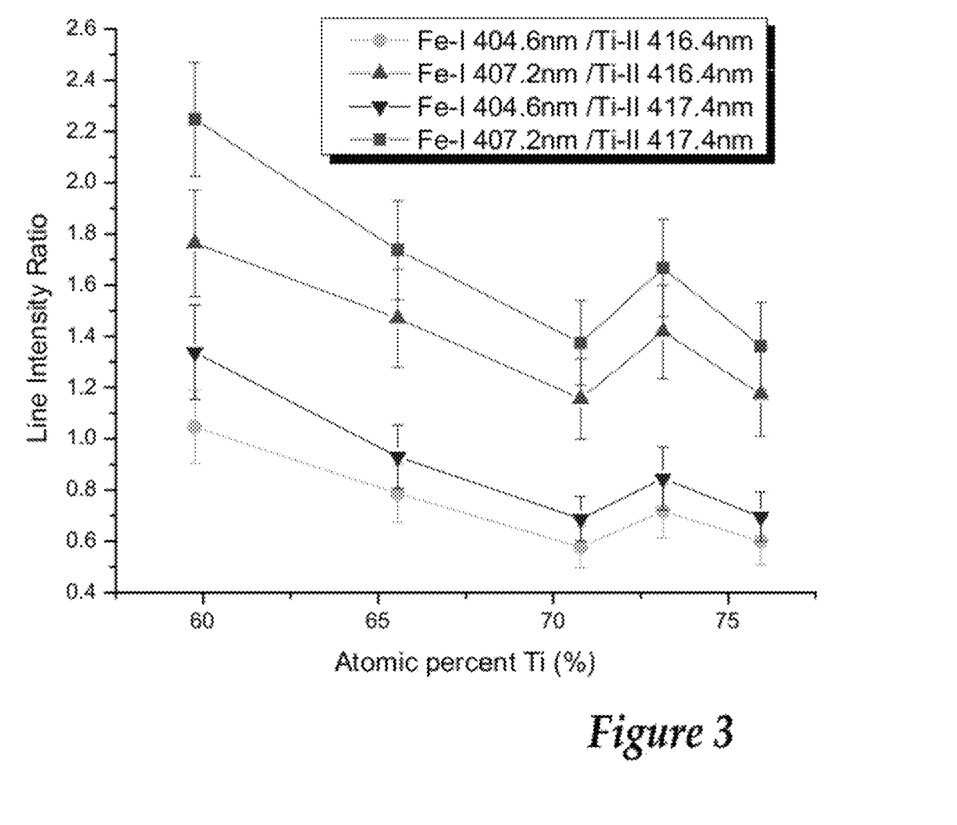
FIG. 3 is a graph depicting the relationship between four Fe-I/Ti-II line ratios and Ti atomic percentages.
Figure 4:
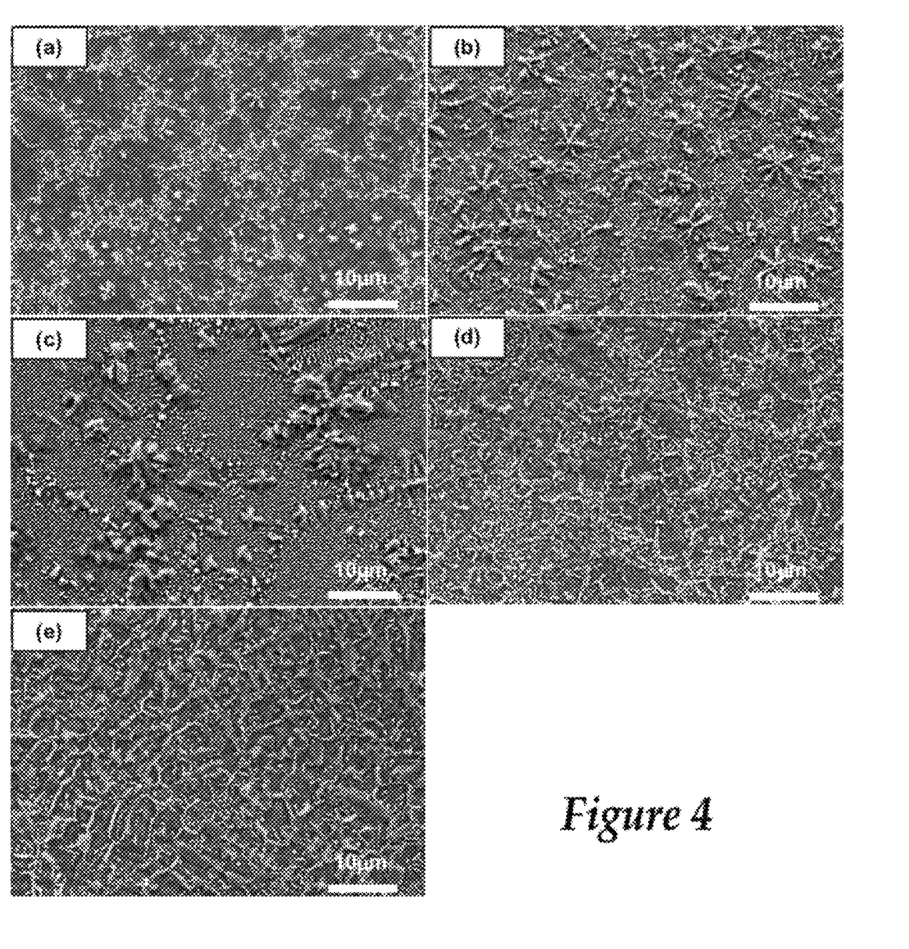
FIG. 4 shows images of SEM morphologies of Ti—Fe alloys with different compositions: (a) $Ti_{75.9}Fe_{24.1}$, (b) $Ti_{73.1}Fe_{26.9}$, (c) $Ti_{70.8}Fe_{29.2}$, (d) $Ti_{65.5}Fe_{34.4}$ and (e) $Ti_{59.8}Fe_{40.2}$.

FIG. 3 shows the relationship between Fe-I/Ti-II spectral line intensity ratio and titanium concentration. The two neutral iron lines are Fe-I 404.58 nm and Fe-I 407.17 nm, both with transition configuration of $3d^7(^4F)4s$–$3d^7(^4F)4p$. The two singly ionized titanium lines are Ti-II 416.36 nm and Ti-II 417.41 nm, both with transition configuration of $3d^3$–$3d^2(^3P)4p$. The separation of the two decreasing line is at $Ti_{71}Fe_{29}$, where eutectic microstructure is obtained. The left side of the eutectic point is hypereutectic phase, where the Fe/Ti line intensity ratio is reverse proportional to the atomic percentage of Ti. The Fe/Ti line intensity ratio jumps up from eutectic point to hypoeutectic region and forms a second decreasing line with the increase of Ti concentration. FIG. 4 shows SEM morphologies of the Ti—Fe alloys with different composition. A primary dendrite of the TiFe phase with B2 CsCl-type structure is formed in the hypereutectic alloys. Dendrite's decreases with the decrease of Fe content. The hypoeutectic alloys is featured with a small-volume fraction of β-Ti+TiFe eutectic distributing at the boundaries of the β-Ti solid solution grains. In the β-Ti solid solution grains a primary dendrite of the β-Ti phase is formed. The microstructure of the eutectic alloy consists of a fishbone-like β-Ti+TiFe eutectic with the average interlamellar spacing of 0.6 μm. The disperse TiFe (light color) phase is a leading eutectic phase in the eutectic, while β-Ti solid solution is formed between the TiFe eutectic phases. Since Fe is known as a β-Ti stabilizer, Fe helps to preserve the non-equilibrium β-Ti and TiFe phases. The disordered bcc β-Ti solid solution is an A2 phase with Fe atoms randomly substituting Ti atoms. An oxygen stabilized $Ti_2Fe$ phase with an average size of 8 μm is also found at the interface of the eutectic cell. XRD analysis also confirmed diffraction peaks corresponding to face-centered cubic $Ti_4Fe_2O$ phase since titanium is famous for attracting oxygen. The content of oxygen-stabilized $Ti_2Fe$ intermetallics decreases with the decreasing of Fe content. The two decreasing lines correspond to bcc-based B2 phase and bcc-based A2 phase respectively.

Figure 5:
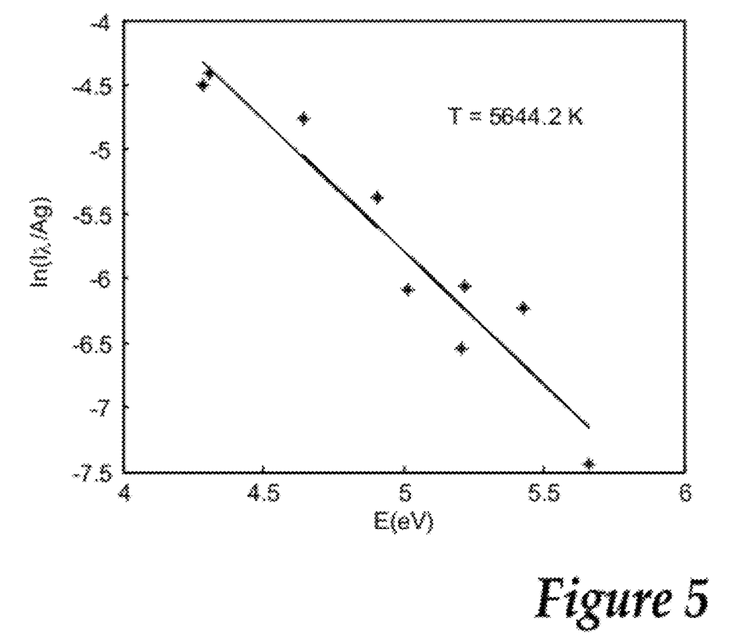
FIG. 5 is a Boltzmann plot from nine Ti-II lines during laser cladding of binary powers with composition atomic ratio of $Ti_{59.8}/Fe_{40.2}$.
Figure 6:
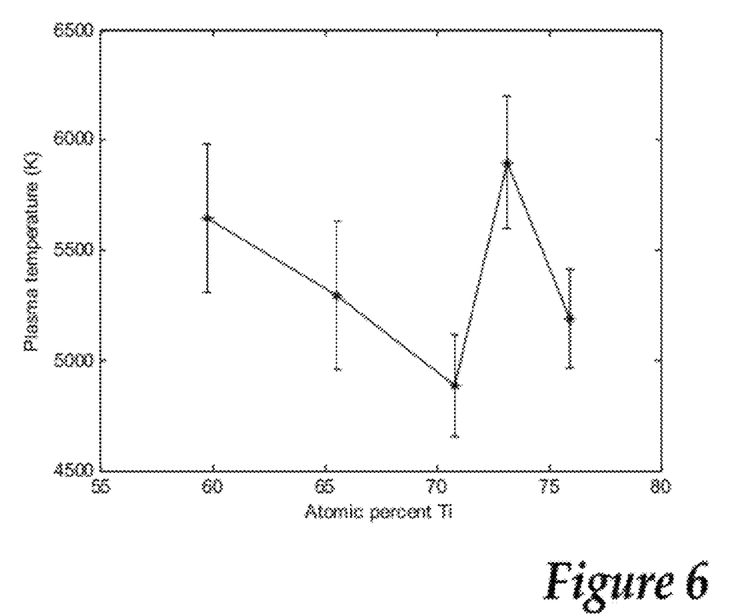
FIG. 6 shows plasma temperature for different Ti atomic percentages.

The electron temperature can be calculated from the slope of this linear function (Eq. (3)) by generating a Boltzmann plot from nine Ti-II lines. Table 1 is a summary of the atomic parameters for the chosen Ti-II lines from NIST database. One example of the Boltzmann plot of the nine Ti-II lines during laser cladding of $Ti_{59.8}Fe_{40.2}$ is shown in FIG. 5. The plasma temperature can be obtained from the slope of the fitted line based on Eq. (3). FIG. 6 shows the plasma temperature during laser cladding with powders of different Ti/Fe atomic ratios, after averaging the time domain results. The plasma temperature at the eutectic composition is lower than the two immediate neighbors.

TABLE 1

| Element | λ (nm) | $A_{mn}$ (Sec$^{-1}$) | $\Delta A_{mn}$ (%) | $E_n$ (eV) | $E_m$ (eV) | $g_m$ |
|---|---|---|---|---|---|---|
| Ti-II | 310.508 | 6.3e+07 | 50 | 1.22406 | 5.215831 | 4 |
| | 311.767 | 1.1e+08 | 25 | 1.23125 | 5.206911 | 2 |
| | 327.829 | 9.6e+07 | 25 | 1.23125 | 5.012134 | 4 |
| | 328.766 | 1.4e+08 | 25 | 1.892696 | 5.662807 | 10 |
| | 350.489 | 8.2e+07 | 50 | 1.891680 | 5.428126 | 10 |
| | 362.482 | 2.9e+07 | 40 | 1.22136 | 4.640800 | 2 |
| | 370.623 | 3.1e+07 | 40 | 1.565763 | 4.910115 | 4 |
| | 390.054 | 1.6e+07 | 40 | 1.13052 | 4.308252 | 10 |
| | 391.346 | 1.6e+07 | 40 | 1.11557 | 4.282818 | 8 |

Figure 7:
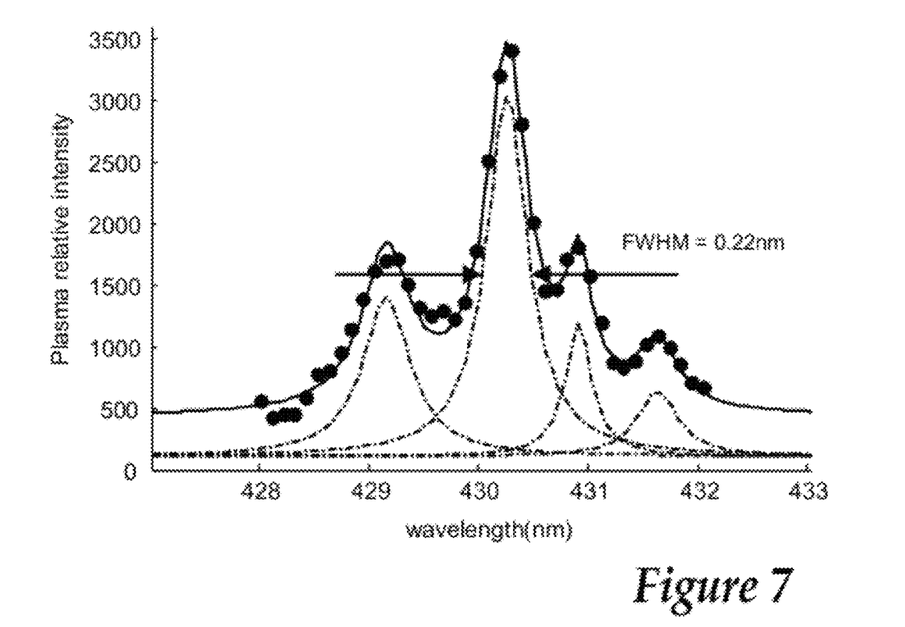
FIG. 7 shows fitting of the spectral line to Lorentz function and obtaining the Full Width Half Maxima (FWHM)
Figure 8:
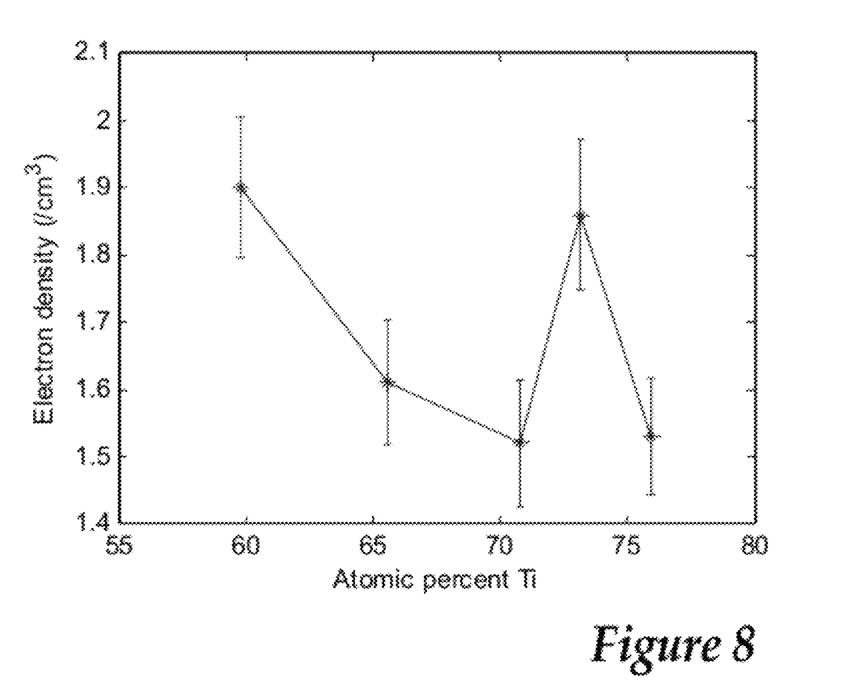
FIG. 8 shows how variations of electron densities correspond to different Ti atomic percentages.

The electron density can be obtained using Eq. (5) by fitting the spectral line to Lorentz function and obtaining the FWHM of the fitted line, as shown in FIG. 7. FIG. 8 shows the relationship between the electron densities and the Ti/Fe atomic ratios. The trend of the electron densities resembles the trend of the plasma temperature. A similar singular point is located at $Ti_{70.8}Fe_{29.2}$ composition. To validate the local thermodynamic equilibrium (LTE) condition, McWhirter criterion of Eq. (5) is used. For Fe-I line ΔE=2.8831 eV. At high temperature (T~6000K), $N_e$=2.97×10$^{15}$ cm$^{-3}$, which ensures the validity of LTE conditions.

Example 2

Ni—Al Alloy

Figure 9:
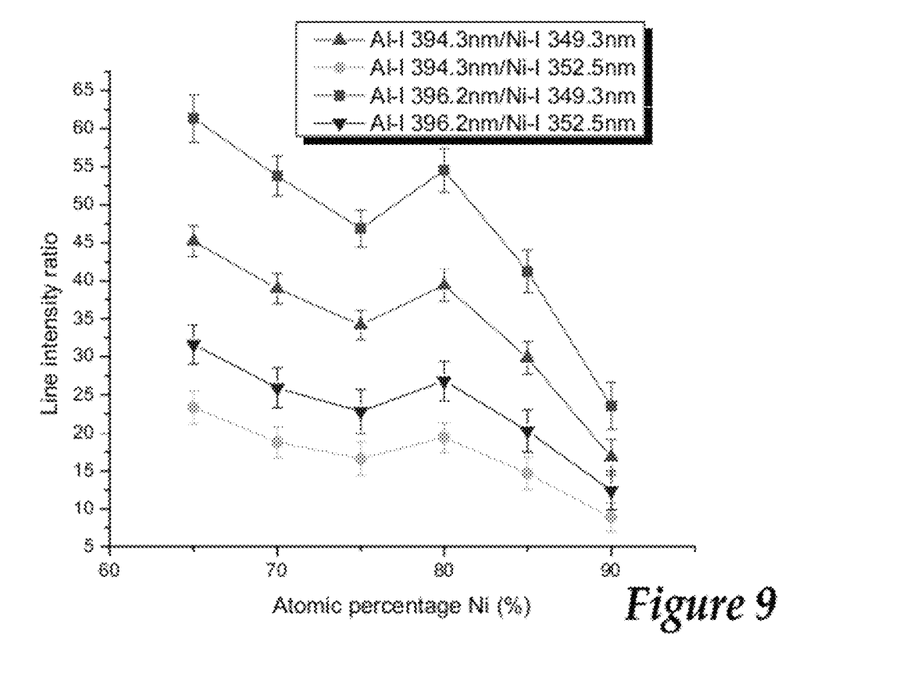
FIG. 9 is a graph depicting the relationship between four Al-I/Ni-I line ratios and Ni atomic percentages.
Figure 10:
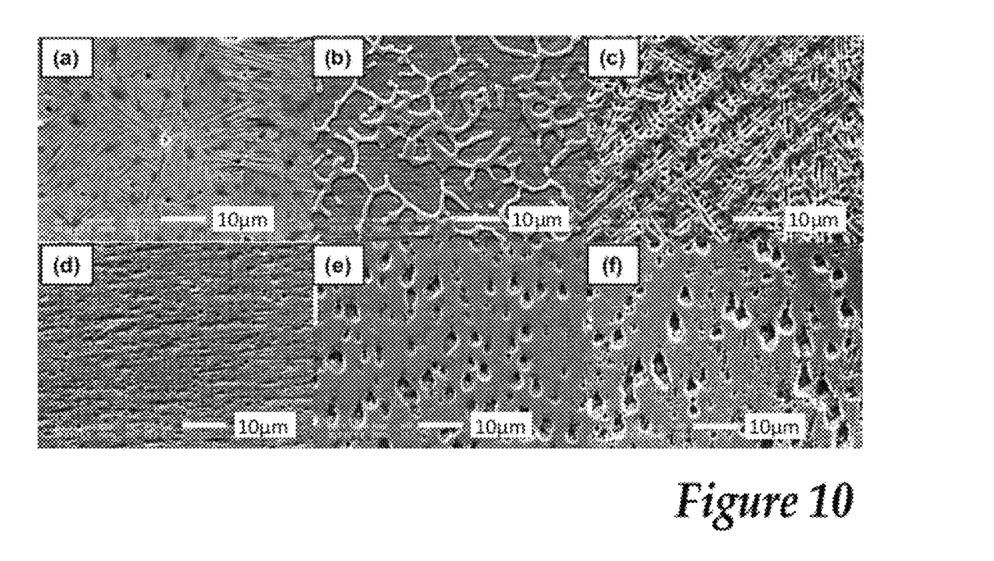
FIG. 10 shows images of SEM morphologies of Ni—Al alloys with different compositions: (a) $Ni_{65}Al_{35}$, (b) $Ni_{70}Al_{30}$, (c) $Ni_{75}Al_{25}$, (d) $Ni_{80}Al_{20}$, (e) $Ni_{85}Al_{15}$, and (f) $Ni_{90}Al_{10}$.

Similar experiments were performed for Ni—Al alloy. All the parameters were kept the same except this time a 700 W laser power was used and $Ni_{75}Al_{25}$ powder flow rate of 6.3 grams per minute. The relationship between the Al-I/Ni-I line intensity ratios and the nickel atomic percentage is shown in FIG. 9. The two neutral aluminum lines are Al-I 394.4 nm and Al-396.15 nm, both with the transition configuration of $3s^23p$–$3s^24s$. The two neutral nickel lines are Ni-I 349.296 nm and Ni-I 352.454 nm, both with transition configuration of $3d^9(^2D)4s$–$3d^9(^2D)4p$. Two decreasing line intensity ratio curves are formed as nickel atomic concentration increases. The first decreasing line stops at 75% nickel atomic percentage. The second decreasing line starts at 80% nickel atomic percentage where Al/Ni line intensity ratio jumps up even though Al concentration decreases. The microstructure for each nickel aluminum composition is shown in FIG. 10. Corresponding to the first decreasing line, a primary nickel rich dendrite develops and grows as nickel contents increase up to 75%. XRD patterns show that these alloys contain both $AlNi_3$ and AlNi phases with bcc-based CsCl-type B2 structure. In this range, the spectral line intensity ratio between aluminum and nickel decreases as nickel content increases, which matches composition changes. Corresponding to the starting point of second decreasing line where the atomic percentage of nickel is 80%, $Ni_3Al$ γ' phase with $L1_2$ structure is developed in the nickel rich matrix. The microstructures of both $Al_{15}Ni_{85}$ and $Al_{10}Ni_{90}$ are similar to nickel matrix with A1 nickel structure with Al atoms randomly substituting Ni atoms. Two decreasing line correspond to two different types of phases. And within each phase, the line intensity ratio is proportional to elemental concentrations. The abnormal change of the line intensity ratio at Ni atomic percentage of 80% indicates the formation of a new phase.

Example 3

Ni—Ti Alloy

Figure 11:
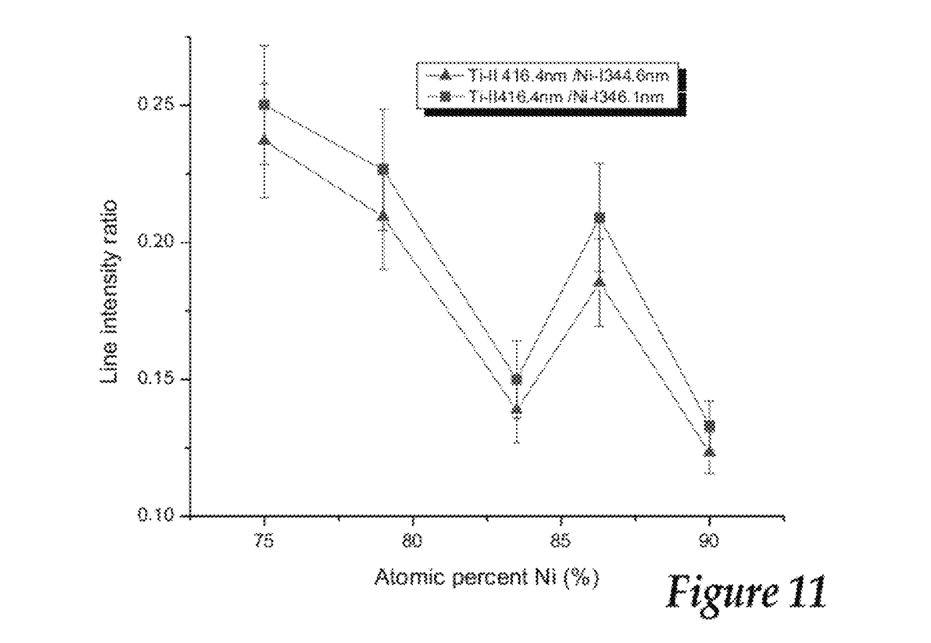
FIG. 11 is a graph depicting the relationship between four Ti-II/Ni-I line ratios and Ni atomic percentages.
Figure 12:
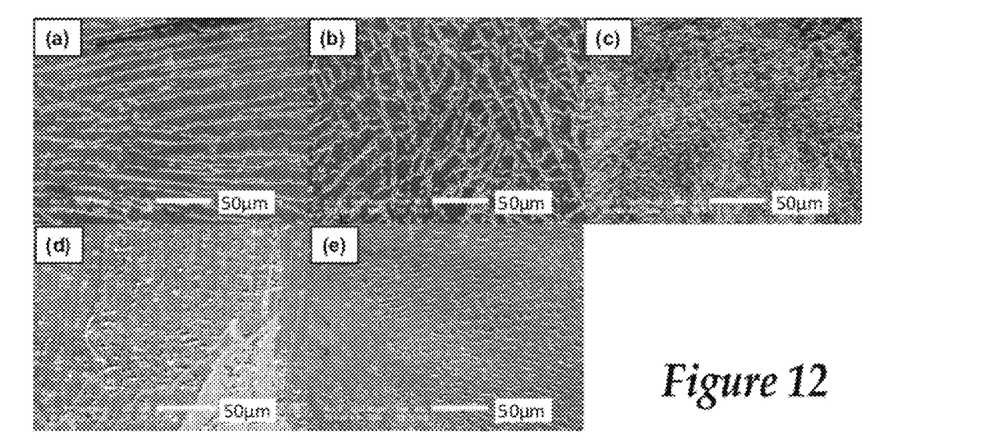
FIG. 12 shows images of SEM morphologies of Ni—Ti alloys with different compositions: (a) $Ni_{75}Ti_{25}$, (b) $Ni_{79}Ti_{21}$, (c) $Ni_{83.5}Ti_{16.5}$, (d) $Ni_{87.3}Ti_{13.7}$, and (e) $Ni_{90}Ti_{10}$.

Similar experiments were performed for Ni—Ti alloy. All the parameters were kept the same as in Ni—Al experiment except the powder flow rate from $Ni_{90}Ti_{10}$ is 8.0 grams per minute. FIG. 11 shows the relationship between Ti-II/Ni-I spectral line intensity ratio and the Ni atomic percentage in the synthesized materials. The singly ionized titanium line is Ti-II 416.36 nm with transition configuration of $3d^3$–$3d^2$ ($^3P$)4p. The two neutral nickel lines are Ni-I 344.626 nm with transition configuration of $3d^9(^2D)_4s$–$3d^9(^2D)4p$ and Ni-I 346.165 nm with transition configuration of $3d^9(^2D)4s$–$3d^8(^3F)4s4p(^3P°)$. Similar to Ni—Al and Ti—Fe synthesizing process, two decreasing lines are formed as Ni concentration increases. FIG. 12 shows SEM morphologies of Ni—Ti alloys with different Ni—Ti compositions. Primary dendrites of $Ni_3Ti$ phase with a $D0_{24}$ structure are formed for $Ni_{75}Ti_{25}$, $Ni_{79}Ti_{21}$ and $Ni_{84}Ti_{16}$ alloys. Both dendrite size and length decrease with the increase of Ni contents. Both $Ni_{87}Ti_{13}$ and $Ni_{90}Ti_{10}$ alloys are distorted A1 nickel structures with occasionally observed γ' $Ni_3Ni$ phase with $L1_2$ structure under SEM analysis. The two decreasing lines correspond to the two different types of microstructures.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A method of determining a microstructure of a material during phase transformation of the material, comprising the steps of:
   (a) detecting light emitted from a plasma plume created during phase transformation of a material;
   (b) determining at least some of the spectral content of the detected light; and
   (c) determining, from the determined spectral content, spectral data representing one or more spectral parameters; and
   (d) determining an expected microstructure including a crystal structure of the transformed material from the determined spectral data.

2. The method of claim 1, wherein the phase transformation of a material in step (a) comprises an alloying of at least two different materials, and wherein step (c) further comprises, for each of at least two of the different materials, determining from the spectral content at least one spectral line associated with that material, and thereafter determining the microstructure based at least in part on the relative line intensities of the determined spectral lines.

3. The method of claim 2, wherein step (c) further comprises determining the relative amount of the different materials based on the determined spectral lines.

4. The method of claim 1, wherein step (c) further comprises determining electron temperature from the determined spectral content and determining the microstructure based at least in part on the electron temperature.

5. The method of claim 1, wherein step (c) further comprises determining electron density from the determined spectral content and determining the microstructure based at least in part on the electron density.

6. The method of claim 5, wherein the electron density is determined based on line broadening of one or more spectral lines contained in the determined spectral content.

7. The method of claim 6, wherein the electron density is determined based at least in part on Stark broadening of the one or more spectral lines.

8. The method of claim 1, wherein step (c) further comprises determining a plurality of parameters from the determined spectral content, and thereafter determining the microstructure based on the parameters.

9. The method of claim 8, wherein the parameters include electron temperature, electron density, and spectral line intensities.

10. The method of claim 1, wherein step (a) further comprises detecting light emitted from a plasma plume created by phase transformation of the material.

11. The method of claim 10, wherein step (a) further comprises detecting light emitted from a plasma plume created by a laser cladding or laser alloying process.

12. The method of claim 1, wherein step (a) further comprises detecting light emitted from a plasma plume created by interaction of injected energy with the material.

13. A microstructure detector for use during phase transformation of a material, comprising:
   a light collector oriented to receive light emitted from a plasma plume created during phase transformation of a material;
   a sensor that receives the light from said light collector, said sensor including a photo-detector operable to output spectral data indicative of at least some of the spectral content of the received light; and
   a computing device that receives the spectral data from said sensor, said computing device operating to determine an expected microstructure including a crystal structure of the transformed material from the received spectral data.

14. A microstructure detector as set forth in claim 13, wherein said computing device operates to determine one or more spectral parameters from the spectral data and determine the microstructure based on the one or more spectral parameters.

15. A microstructure detector as set forth in claim 14, wherein the one or more spectral parameters include one or more of the following: electron temperature, electron density, and spectral line intensities.

16. A microstructure detector as set forth in claim 14, wherein the one or more spectral parameters comprise electron temperature, electron density, and spectral line intensities, and wherein said computing device operates to determine the microstructure based at least in part on all three spectral parameters.

17. A computer-controlled phase transformation system comprising a phase transformation controller and the microstructure detector of claim 13, wherein said computing device provides feedback that is inputted to said phase transformation controller, and wherein said phase transformation controller operates to carry out the phase transformation of the material and operates to adjust one or more of process parameters during the phase transformation based on the feedback received from said microstructure detector.

* * * * *